United States Patent
Cooney et al.

(10) Patent No.: US 9,422,541 B2
(45) Date of Patent: Aug. 23, 2016

(54) APPARATUS FOR THE EXTRACORPOREAL TREATMENT OF BLOOD

(71) Applicant: University of Limerick, Limerick (IE)

(72) Inventors: Jakki Cooney, Mallow (IE); Todd Fumio Kagawa, Kailua, HI (US); Edmond Magner, Drombanna (IE)

(73) Assignee: University of Limerick, Limerick (IE)

( * ) Notice: Subject to any disclaimer, the term of this patent is extended or adjusted under 35 U.S.C. 154(b) by 0 days.

(21) Appl. No.: 14/314,387

(22) Filed: Jun. 25, 2014

(65) Prior Publication Data
US 2015/0166978 A1 Jun. 18, 2015

(30) Foreign Application Priority Data
Dec. 17, 2013 (EP) .................................. 13197790

(51) Int. Cl.
| | | |
|---|---|---|
| *A61M 1/36* | (2006.01) | |
| *C12N 9/52* | (2006.01) | |
| *C12N 11/14* | (2006.01) | |
| *A61L 33/00* | (2006.01) | |
| *A61M 1/34* | (2006.01) | |

(52) U.S. Cl.
CPC ............. *C12N 11/14* (2013.01); *A61L 33/0047* (2013.01); *A61M 1/3496* (2013.01); *A61M 1/3687* (2013.01); *A61M 1/3689* (2014.02); *C12N 9/52* (2013.01); *C12Y 304/2111* (2013.01)

(58) Field of Classification Search
None
See application file for complete search history.

(56) References Cited

U.S. PATENT DOCUMENTS

| | | | | |
|---|---|---|---|---|
| 5,817,042 | A * | 10/1998 | Langley et al. | 604/6.07 |
| 2003/0003223 | A1 * | 1/2003 | Morse et al. | 427/2.11 |
| 2012/0109039 | A1 * | 5/2012 | Hyde et al. | 604/6.15 |

FOREIGN PATENT DOCUMENTS

| | | |
|---|---|---|
| WO | WO-95125540 | 9/1995 |
| WO | WO-2010/036960 | 4/2010 |

OTHER PUBLICATIONS

Wexler, D. E., et al., 1985, "Mechanism of action of the group A streptococcal C5a inactivator", Proceedings of the National Academy of Sciences, U.S.A., vol. 82, pp. 8144-8148.*
Cleary, P., et al., 1992, "Streptococcal C5a peptidase is a highly specific endopeptidase", Infection and Immunity, vol. 60, No. 12, pp. 5219-5223.*
Toth, M.J., et al., 1994, "The pharmacophore of the human C5a anaphylatoxin", Protein Science, vol. 3, pp. 1159-1168.*
(Continued)

*Primary Examiner* — Manjunath Rao
*Assistant Examiner* — William W Moore
(74) *Attorney, Agent, or Firm* — Cesari and McKenna LLP

(57) ABSTRACT

An apparatus for the extracorporeal treatment of blood comprising an extracorporeal blood circuit (2), a pump (6) configured to provide fluid displacement within the extracorporeal blood circuit, and a reaction chamber (8) connected to the extracorporeal blood circuit and configured to receive blood or plasma from the circuit and treat the blood or plasma. The reaction chamber comprises an protease enzyme immobilized to a support, in which the protease enzyme is specific for, and capable of irreversibly cleaving, a human C5a present in the blood or plasma, wherein the abundance of the human C5a in the treated blood or plasma is less than that in the untreated blood or plasma. The apparatus finds utility in the extracorporeal treatment of blood from patients with inflammatory conditions, especially auto-immune disease and sepsis.

13 Claims, 2 Drawing Sheets

(56) References Cited

OTHER PUBLICATIONS

Cheng, Q., et al., 2002, "The group B streptococcal C5a peptidase is both a specific protease and an invasin", Infection and Immunity, vol. 70, No. 5, pp. 2408-2413.*

Brown, C.K., et al., 2005, "Structure of the streptococcal cell wall C5a peptidase", Proceedings of the National Academy of Sciences, U.S.A., vol. 102, No. 51, pp. 18391-18396.*

Brown, C.K., et al., 2006, "The structure of the cell-wall protease from streptococci that inactivates the human complement factor 5a", International Congress Series, vol. 1289, pp. 211-215.*

Ji Y., et al., 1996, "C5a peptidase alters clearance and trafficking of Group A streptococci by infected mice", Infection and Immunity, vol. 64, No. 2, pp. 503-510.*

Cunningham, M. W., 2000, "Pathogenesis of Group A streptococcal infections", Clinical Microbiology Reviews, vol. 13, No. 3, pp. 470-511.*

Terao, Y., 2012, "The virulence factors and pathogenic mechanisms of *Streptococcus pyogenes*", Journal of Oral Biosciences, vol. 54, No. 1, pp. 96-100.*

Horst, S.A., et al., 2013, "Prognostic value and therapeutic potential of TREM-1 in *Streptococcus pyogenes*-induced sepsis", Journal of Innate Immunity, vol. 5, pp. 581-590.*

Kawaga, et al., "Model for substrate interactions in C5a peptidase from *Streptococcus pyogenes*. A 1.9 A crystal structure of the active form of ScpA", Journal of Molecular Biology, vol. 386, No. 3, Feb. 2009.

* cited by examiner (a)

Δ830 DA

− +

(b)

| P4 | P3 | P2 | P1 | ↓ | P1' | P2' |
|---|---|---|---|---|---|---|
| N64$_s$ | I65$_s$ | S66$_s$ | H67$_s$ | ⋯ | K68$_s$ | D69$_s$ |

SEQUENCE LISTING

```
<160> NUMBER OF SEQ ID NOS: 6

<210> SEQ ID NO 1
<211> LENGTH: 3015
<212> TYPE: DNA
<213> ORGANISM: Streptococcus pyogenes
<220> FEATURE:
<221> NAME/KEY: misc_feature
<222> LOCATION: (1)..(3015)
<223> OTHER INFORMATION: Gene encoding ScpA

<400> SEQUENCE: 1
ggatccaata ctgtgacaga agacactcct gctaccgaac aagccgtaga aaccccacaa      60
ccaacagcgg tttctgagga agcaccatca tcatcaaagg aaaccaaaat cccacaaact     120
cctggtgatg cagaagaaac agtagcagat gacgctaatg atctagcccc tcaagctcct     180
gctaaaactg ctgatacacc agcaacctca aaagcgacta ttagggattt gaacgaccct    240
```

```
tctcaggtca aaaccctgca ggaaaaagca ggcaagggag ctgggactgt tgttgcagtg    300
attgatgctg gttttgataa aaatcatgaa gcgtggcgct taacagacaa aactaaagca    360
cgttaccaat caaaagaaga tcttgaaaaa gctaaaaaag agcacggtat tacctatggc    420
gagtgggtca atgataaggt tgcttattac cacgattata gtaaagatgg taaaaccgct    480
gtcgatcaag agcacggcac acacgtgtca gggatcttgt caggaaatgc tccatctgaa    540
acgaaagaac cttaccgcct agaaggtgcg atgcctgagg ctcaattgct tttgatgcgt    600
gtcgaaattg taaatggact agcagactat gctcgtaact acgctcaagc tatcagagat    660
gctgtcaact gggagctaaa ggtgattaat atgagctttg gtaatgctgc actagcttac    720
gccaaccttc cagacgaaac caaaaaagcc tttgactatg ccaaatcaaa aggtgttagc    780
attgtgacct cagctggtaa tgatagtagc tttgggggca aaacccgtct acctctagca    840
gatcatcctg attatggggt ggttgggacg cctgcagcgg cagactcaac attgacagtt    900
gcttcttaca gcccagataa acagctcact gaaactgcta cggtcaaaac agacgatcat    960
caagctaaag aaatgcctgt tctttcaaca aaccgttttg agccaaacaa ggcttacgac   1020
tatgcttatg ctaatcgtgg gatgaaagaa gatgatttta aggatgtcaa aggcaaaatt   1080
gcccttattg aacgtggtga tattgatttc aaagataaga ttgcaaacgc taaaaaagct   1140
ggtgctgtag ggtcttgat ctatgacaat caagacaagg gcttcccgat tgaattgcca   1200
aatgttgatc agatgcctgc ggcctttatc agtcgaaaag acggtctctt attaaaagac   1260
aattctaaaa aaaccatcac cttcaatgcg acacctaagg tattgccaac agcaagtgac   1320 accaaaactaa gccgcttctc aagctggggt ttgacagctg acggcaatat taagccagat   1380
attgcagcac ccggccaaga tattttgtca tcagtggcta acaacaagta tgccaaactt   1440
tctggaacta gtatgtctgc gccattggta gcgggtatca tgggactatt gcaaaagcaa   1500
tatgagacac agtatcctga tatgacacca tcagagcgtc ttgatttagc taaaaaagta   1560
ttgatgagct cagcaactgc cttatatgat gaagatgaaa aagcttattt ttctcctcgc   1620
caacaaggag caggagcagt cgatgctaaa aaagcttcag cagcaacgat gtatgtgaca   1680
gataaggaca atacctcaag caaggttcac ctgaacaatg tttctgataa atttgaagta   1740
acagtaacag ttcacaacaa atctgataaa cctcaagagt tgtattacca agcaactgtt   1800
caaacagata agtagatgg aaaacacttt gccttggctc ctaaagcatt gtatgagaca   1860
tcatggcaaa aaatcacaat tccagccaat agcagcaaac aagtcaccgt tccaatcgat   1920
gctagtcgat ttagcaagga cttgcttgcc caaatgaaaa atggctattt cttagaaggt   1980
tttgttcgtt tcaaacaaga tcctaaaaaa gaagagctta tgagcattcc atatattggt   2040
ttccgaggtg attttggcaa tctgtcagcc ttagaaaaac caatctatga tagcaaagac   2100
ggtagcagct actatcatga agcaaatagt gatgccaaag accaattaga tggtgatgga   2160
ttacagtttt acgctctgaa aaataacttt acagcactta ccacagagtc taacccatgg   2220
acgattatta agctgtcaa agaagggatt gaaaacatag aggatatcga atcttcagag   2280
atcacagaaa ccatttttgc aggtactttt gcaaacaag acgatgatag ccactactat   2340
atccaccgtc acgctaatgg caaaccatat gctgcgatct ctccaaatgg ggacggtaac   2400
agagattatg tccaattcca aggtactttc ttgcgtaatg ctaaaaacct tgtggctgaa   2460
gtcttggaca aagaaggaaa tgttgtttgg acaagtgagg taaccgagca agttgttaaa   2520
aactacaaca atgacttggc aagcacactt ggttcaaccc gttttgaaaa aacgcgttgg   2580
gacggtaaag ataaagacgg caaagttgtt gttaacggaa cctacaccta tcgtgtccgc   2640
```

```
tacactccga ttagctcagg tgcaaaagaa caacacactg attttgatgt gattgtagac   2700
aatacgacac ctgaagtcgc aacatcggca acattctcaa cagaagatcg tcgtttgaca   2760
cttgcatcta aaccaaaaac cagccaaccg atttaccgtg agcgtattgc ttacacttat   2820
atggatgagg atctgccaac aacagagtat atttctccaa atgaagatgg tacctttact   2880
cttcctgaag aggctgaaac aatggaaggc ggtactgttc cattgaaaat gtcagacttt   2940
acttatgttg ttgaagatat ggctggtaac atcacttata caccagtgac taagctattg   3000
gagggccact cttaa                                                    3015
```

<210> SEQ ID NO 2
<211> LENGTH: 1007
<212> TYPE: PRT
<213> ORGANISM: Streptococcus pyogenes
<220> FEATURE:
<221> NAME/KEY: MISC_FEATURE
<222> LOCATION: (1)..(1007)
<223> OTHER INFORMATION: ScpA pro-protease

<400> SEQUENCE: 2

```
Gly Pro Leu Gly Ser Asn Thr Val Thr Glu Asp Thr Pro Ala Thr Glu
1               5                   10                  15

Gln Ala Val Glu Thr Pro Gln Pro Thr Ala Val Ser Glu Glu Ala Pro
            20                  25                  30

Ser Ser Ser Lys Glu Thr Lys Ile Pro Gln Thr Pro Gly Asp Ala Glu
        35                  40                  45

Glu Thr Val Ala Asp Asp Ala Asn Asp Leu Ala Pro Gln Ala Pro Ala
    50                  55                  60

Lys Thr Ala Asp Thr Pro Ala Thr Ser Lys Ala Thr Ile Arg Asp Leu
65                  70                  75                  80

Asn Asp Pro Ser Gln Val Lys Thr Leu Gln Glu Lys Ala Ser Lys Gly
                85                  90                  95

Ala Gly Thr Val Val Ala Val Ile Asp Ala Gly Phe Asp Lys Asn His
            100                 105                 110

Glu Ala Trp Arg Leu Thr Asp Lys Thr Lys Ala Arg Tyr Gln Ser Lys
        115                 120                 125

Glu Asp Leu Glu Lys Ala Lys Lys Glu His Gly Ile Thr Tyr Gly Glu
    130                 135                 140

Trp Val Asn Asp Lys Val Ala Tyr Tyr His Asp Tyr Ser Lys Asp Gly
145                 150                 155                 160

Lys Thr Ala Val Asp Gln Glu His Gly Thr His Val Ser Gly Ile Leu
                165                 170                 175

Ser Gly Asn Ala Pro Ser Glu Thr Lys Glu Pro Tyr Arg Leu Glu Gly
            180                 185                 190

Ala Met Pro Glu Ala Gln Leu Leu Leu Met Arg Val Glu Ile Val Asn
        195                 200                 205

Gly Leu Ala Asp Tyr Ala Arg Asn Tyr Ala Gln Ala Ile Arg Asp Ala
    210                 215                 220

Val Asn Leu Gly Ala Lys Val Ile Asn Met Ser Phe Gly Asn Ala Ala
225                 230                 235                 240

Leu Ala Tyr Ala Asn Leu Pro Asp Glu Thr Lys Lys Ala Phe Asp Tyr
                245                 250                 255

Ala Lys Ser Lys Gly Val Ser Ile Val Thr Ser Ala Gly Asn Asp Ser
            260                 265                 270

Ser Phe Gly Gly Lys Thr Arg Leu Pro Leu Ala Asp His Pro Asp Tyr
```

```
                 275                 280                 285
Gly Val Val Gly Thr Pro Ala Ala Asp Ser Thr Leu Thr Val Ala
290                 295                 300
Ser Tyr Ser Pro Asp Lys Gln Leu Thr Glu Thr Ala Thr Val Lys Thr
305                 310                 315                 320
Asp Asp His Gln Ala Lys Glu Met Pro Val Leu Ser Thr Asn Arg Phe
                325                 330                 335
Glu Pro Asn Lys Ala Tyr Asp Tyr Ala Tyr Ala Asn Arg Gly Met Lys
                340                 345                 350
Glu Asp Asp Phe Lys Asp Val Lys Gly Lys Ile Ala Leu Ile Glu Arg
                355                 360                 365
Gly Asp Ile Asp Phe Lys Asp Lys Ile Ala Asn Ala Lys Lys Ala Gly
370                 375                 380
Ala Val Gly Val Leu Ile Tyr Asp Asn Gln Asp Lys Gly Phe Pro Ile
385                 390                 395                 400
Glu Leu Pro Asn Val Asp Gln Met Pro Ala Ala Phe Ile Ser Arg Lys
                405                 410                 415
Asp Gly Leu Leu Leu Lys Asp Asn Ser Lys Lys Thr Ile Thr Phe Asn
                420                 425                 430
Ala Thr Pro Lys Val Leu Pro Thr Ala Ser Asp Thr Lys Leu Ser Arg
                435                 440                 445
Phe Ser Ser Trp Gly Leu Thr Ala Asp Gly Asn Ile Lys Pro Asp Ile
450                 455                 460
Ala Ala Pro Gly Gln Asp Ile Leu Ser Ser Val Ala Asn Asn Lys Tyr
465                 470                 475                 480
Ala Lys Leu Ser Gly Thr Ser Met Ser Ala Pro Leu Val Ala Gly Ile
                485                 490                 495
Met Gly Leu Leu Gln Lys Gln Tyr Glu Thr Gln Tyr Pro Asp Met Thr
                500                 505                 510
Pro Ser Glu Arg Leu Asp Leu Ala Lys Lys Val Leu Met Ser Ser Ala
                515                 520                 525
Thr Ala Leu Tyr Asp Glu Asp Glu Lys Ala Tyr Phe Ser Pro Arg Gln
530                 535                 540
Gln Gly Ala Gly Ala Val Asp Ala Lys Lys Ala Ser Ala Ala Thr Met
545                 550                 555                 560
Tyr Val Thr Asp Lys Asp Asn Thr Ser Ser Lys Val His Leu Asn Asn
                565                 570                 575
Val Ser Asp Lys Phe Glu Val Thr Val Thr Val His Asn Lys Ser Asp
                580                 585                 590
Lys Pro Gln Glu Leu Tyr Tyr Gln Ala Thr Val Gln Thr Asp Lys Val
                595                 600                 605
Asp Gly Lys His Phe Ala Leu Ala Pro Lys Ala Leu Tyr Glu Thr Ser
                610                 615                 620
Trp Gln Lys Ile Thr Ile Pro Ala Asn Ser Ser Lys Gln Val Thr Val
625                 630                 635                 640
Pro Ile Asp Ala Ser Arg Phe Ser Lys Asp Leu Leu Ala Gln Met Lys
                645                 650                 655
Asn Gly Tyr Phe Leu Glu Gly Phe Val Arg Phe Lys Gln Asp Pro Lys
                660                 665                 670
Lys Glu Glu Leu Met Ser Ile Pro Tyr Ile Gly Phe Arg Gly Asp Phe
                675                 680                 685
Gly Asn Leu Ser Ala Leu Glu Lys Pro Ile Tyr Asp Ser Lys Asp Gly
690                 695                 700
```

```
Ser Ser Tyr Tyr His Glu Ala Asn Ser Asp Ala Lys Asp Gln Leu Asp
705                 710                 715                 720

Gly Asp Gly Leu Gln Phe Tyr Ala Leu Lys Asn Asn Phe Thr Ala Leu
            725                 730                 735

Thr Thr Glu Ser Asn Pro Trp Thr Ile Ile Lys Ala Val Lys Glu Gly
        740                 745                 750

Val Glu Asn Ile Glu Asp Ile Glu Ser Ser Glu Ile Thr Glu Thr Ile
    755                 760                 765

Phe Ala Gly Thr Phe Ala Lys Gln Asp Asp Asp Ser His Tyr Tyr Ile
770                 775                 780

His Arg His Ala Asn Gly Lys Pro Tyr Ala Ala Ile Ser Pro Asn Gly
785                 790                 795                 800

Asp Gly Asn Arg Asp Tyr Val Gln Phe Gln Gly Thr Phe Leu Arg Asn
            805                 810                 815

Ala Lys Asn Leu Val Ala Glu Val Leu Asp Lys Glu Gly Asn Val Val
        820                 825                 830

Trp Thr Ser Glu Val Thr Glu Gln Val Val Lys Asn Tyr Asn Asn Asp
    835                 840                 845

Leu Ala Ser Thr Leu Gly Ser Thr Arg Phe Glu Lys Thr Arg Trp Asp
850                 855                 860

Gly Lys Asp Lys Asp Gly Lys Val Val Val Asn Gly Thr Tyr Thr Tyr
865                 870                 875                 880

Arg Val Arg Tyr Thr Pro Ile Ser Ser Gly Ala Lys Glu Gln His Thr
            885                 890                 895

Asp Phe Asp Val Ile Val Asp Asn Thr Thr Pro Glu Val Ala Thr Ser
        900                 905                 910

Ala Thr Phe Ser Thr Glu Asp Arg Arg Leu Thr Leu Ala Ser Lys Pro
    915                 920                 925

Lys Thr Ser Gln Pro Ile Tyr Arg Glu Arg Ile Ala Tyr Thr Tyr Met
930                 935                 940

Asp Glu Asp Leu Pro Thr Thr Glu Tyr Ile Ser Pro Asn Glu Asp Gly
945                 950                 955                 960

Thr Phe Thr Leu Pro Glu Glu Ala Glu Thr Met Glu Gly Gly Thr Val
            965                 970                 975

Pro Leu Lys Met Ser Asp Phe Thr Tyr Val Val Glu Asp Met Ala Gly
        980                 985                 990

Asn Ile Thr Tyr Thr Pro Val Thr  Lys Leu Leu Glu Gly  His Ser
    995                 1000                1005

<210> SEQ ID NO 3
<211> LENGTH: 961
<212> TYPE: PRT
<213> ORGANISM: Streptococcus pyogenes
<220> FEATURE:
<221> NAME/KEY: MISC_FEATURE
<222> LOCATION: (1)..(961)
<223> OTHER INFORMATION: ScpA mature protease

<400> SEQUENCE: 3

Ala Glu Glu Thr Val Ala Asp Asp Ala Asn Asp Leu Ala Pro Gln Ala
1               5                   10                  15

Pro Ala Lys Thr Ala Asp Thr Pro Ala Thr Ser Lys Ala Thr Ile Arg
            20                  25                  30

Asp Leu Asn Asp Pro Ser Gln Val Lys Thr Leu Gln Glu Lys Ala Ser
        35                  40                  45
```

-continued

Lys Gly Ala Gly Thr Val Val Ala Val Ile Asp Ala Gly Phe Asp Lys
 50                  55                  60

Asn His Glu Ala Trp Arg Leu Thr Asp Lys Thr Lys Ala Arg Tyr Gln
 65                  70                  75                  80

Ser Lys Glu Asp Leu Glu Lys Ala Lys Lys Glu His Gly Ile Thr Tyr
                 85                  90                  95

Gly Glu Trp Val Asn Asp Lys Val Ala Tyr Tyr His Asp Tyr Ser Lys
            100                 105                 110

Asp Gly Lys Thr Ala Val Asp Gln Glu His Gly Thr His Val Ser Gly
        115                 120                 125

Ile Leu Ser Gly Asn Ala Pro Ser Glu Thr Lys Glu Pro Tyr Arg Leu
130                 135                 140

Glu Gly Ala Met Pro Glu Ala Gln Leu Leu Met Arg Val Glu Ile
145                 150                 155                 160

Val Asn Gly Leu Ala Asp Tyr Ala Arg Asn Tyr Ala Gln Ala Ile Arg
                165                 170                 175

Asp Ala Val Asn Leu Gly Ala Lys Val Ile Asn Met Ser Phe Gly Asn
            180                 185                 190

Ala Ala Leu Ala Tyr Ala Asn Leu Pro Asp Glu Thr Lys Lys Ala Phe
        195                 200                 205

Asp Tyr Ala Lys Ser Lys Gly Val Ser Ile Val Thr Ser Ala Gly Asn
210                 215                 220

Asp Ser Ser Phe Gly Gly Lys Thr Arg Leu Pro Leu Ala Asp His Pro
225                 230                 235                 240

Asp Tyr Gly Val Val Gly Thr Pro Ala Ala Asp Ser Thr Leu Thr
                245                 250                 255

Val Ala Ser Tyr Ser Pro Asp Lys Gln Leu Thr Glu Thr Ala Thr Val
            260                 265                 270

Lys Thr Asp Asp His Gln Ala Lys Glu Met Pro Val Leu Ser Thr Asn
        275                 280                 285

Arg Phe Glu Pro Asn Lys Ala Tyr Asp Tyr Ala Tyr Ala Asn Arg Gly
290                 295                 300

Met Lys Glu Asp Asp Phe Lys Asp Val Lys Gly Lys Ile Ala Leu Ile
305                 310                 315                 320

Glu Arg Gly Asp Ile Asp Phe Lys Asp Lys Ile Ala Asn Ala Lys Lys
                325                 330                 335

Ala Gly Ala Val Gly Val Leu Ile Tyr Asp Asn Gln Asp Lys Gly Phe
            340                 345                 350

Pro Ile Glu Leu Pro Asn Val Asp Gln Met Pro Ala Ala Phe Ile Ser
        355                 360                 365

Arg Lys Asp Gly Leu Leu Leu Lys Asp Asn Ser Lys Lys Thr Ile Thr
370                 375                 380

Phe Asn Ala Thr Pro Lys Val Leu Pro Thr Ala Ser Asp Thr Lys Leu
385                 390                 395                 400

Ser Arg Phe Ser Ser Trp Gly Leu Thr Ala Asp Gly Asn Ile Lys Pro
                405                 410                 415

Asp Ile Ala Ala Pro Gly Gln Asp Ile Leu Ser Ser Val Ala Asn Asn
            420                 425                 430

Lys Tyr Ala Lys Leu Ser Gly Thr Ser Met Ser Ala Pro Leu Val Ala
        435                 440                 445

Gly Ile Met Gly Leu Leu Gln Lys Gln Tyr Glu Thr Gln Tyr Pro Asp
450                 455                 460

Met Thr Pro Ser Glu Arg Leu Asp Leu Ala Lys Lys Val Leu Met Ser

```
465                 470                 475                 480
Ser Ala Thr Ala Leu Tyr Asp Glu Asp Glu Lys Ala Tyr Phe Ser Pro
                    485                 490                 495

Arg Gln Gln Gly Ala Gly Ala Val Asp Ala Lys Lys Ala Ser Ala Ala
                500                 505                 510

Thr Met Tyr Val Thr Asp Lys Asp Asn Thr Ser Ser Lys Val His Leu
            515                 520                 525

Asn Asn Val Ser Asp Lys Phe Glu Val Thr Val Thr Val His Asn Lys
        530                 535                 540

Ser Asp Lys Pro Gln Glu Leu Tyr Tyr Gln Ala Thr Val Gln Thr Asp
545                 550                 555                 560

Lys Val Asp Gly Lys His Phe Ala Leu Ala Pro Lys Ala Leu Tyr Glu
                565                 570                 575

Thr Ser Trp Gln Lys Ile Thr Ile Pro Ala Asn Ser Ser Lys Gln Val
                580                 585                 590

Thr Val Pro Ile Asp Ala Ser Arg Phe Ser Lys Asp Leu Leu Ala Gln
            595                 600                 605

Met Lys Asn Gly Tyr Phe Leu Glu Gly Phe Val Arg Phe Lys Gln Asp
        610                 615                 620

Pro Lys Lys Glu Glu Leu Met Ser Ile Pro Tyr Ile Gly Phe Arg Gly
625                 630                 635                 640

Asp Phe Gly Asn Leu Ser Ala Leu Glu Lys Pro Ile Tyr Asp Ser Lys
                645                 650                 655

Asp Gly Ser Ser Tyr Tyr His Glu Ala Asn Ser Asp Ala Lys Asp Gln
                660                 665                 670

Leu Asp Gly Asp Gly Leu Gln Phe Tyr Ala Leu Lys Asn Asn Phe Thr
            675                 680                 685

Ala Leu Thr Thr Glu Ser Asn Pro Trp Thr Ile Ile Lys Ala Val Lys
        690                 695                 700

Glu Gly Val Glu Asn Ile Glu Asp Ile Glu Ser Ser Glu Ile Thr Glu
705                 710                 715                 720

Thr Ile Phe Ala Gly Thr Phe Ala Lys Gln Asp Asp Asp Ser His Tyr
                725                 730                 735

Tyr Ile His Arg His Ala Asn Gly Lys Pro Tyr Ala Ala Ile Ser Pro
                740                 745                 750

Asn Gly Asp Gly Asn Arg Asp Tyr Val Gln Phe Gln Gly Thr Phe Leu
            755                 760                 765

Arg Asn Ala Lys Asn Leu Val Ala Glu Val Leu Asp Lys Glu Gly Asn
        770                 775                 780

Val Val Trp Thr Ser Glu Val Thr Glu Gln Val Val Lys Asn Tyr Asn
785                 790                 795                 800

Asn Asp Leu Ala Ser Thr Leu Gly Ser Thr Arg Phe Glu Lys Thr Arg
                805                 810                 815

Trp Asp Gly Lys Asp Lys Asp Gly Lys Val Val Asn Gly Thr Tyr
                820                 825                 830

Thr Tyr Arg Val Arg Tyr Thr Pro Ile Ser Ser Gly Ala Lys Glu Gln
            835                 840                 845

His Thr Asp Phe Asp Val Ile Val Asp Asn Thr Thr Pro Glu Val Ala
        850                 855                 860

Thr Ser Ala Thr Phe Ser Thr Glu Asp Arg Arg Leu Thr Leu Ala Ser
865                 870                 875                 880

Lys Pro Lys Thr Ser Gln Pro Ile Tyr Arg Glu Arg Ile Ala Tyr Thr
                885                 890                 895
```

-continued

Tyr Met Asp Glu Asp Leu Pro Thr Thr Glu Tyr Ile Ser Pro Asn Glu
               900                 905                 910

Asp Gly Thr Phe Thr Leu Pro Glu Glu Ala Glu Thr Met Glu Gly Gly
               915                 920                 925

Thr Val Pro Leu Lys Met Ser Asp Phe Thr Tyr Val Val Glu Asp Met
930                 935                 940

Ala Gly Asn Ile Thr Tyr Thr Pro Val Thr Lys Leu Leu Glu Gly His
945                 950                 955                 960

Ser

<210> SEQ ID NO 4
<211> LENGTH: 954
<212> TYPE: PRT
<213> ORGANISM: Streptococcus pyogenes
<220> FEATURE:
<221> NAME/KEY: MISC_FEATURE
<222> LOCATION: (1)..(954)
<223> OTHER INFORMATION: ScpA protease variant

<400> SEQUENCE: 4

Asp Ala Asn Asp Leu Ala Pro Gln Ala Pro Lys Thr Ala Asp Thr
1                 5                  10                  15

Pro Ala Thr Ser Lys Ala Thr Ile Arg Asp Leu Asn Asp Pro Ser Gln
               20                   25                  30

Val Lys Thr Leu Gln Glu Lys Ala Ser Lys Gly Ala Gly Thr Val Val
               35                   40                  45

Ala Val Ile Asp Ala Gly Phe Asp Lys Asn His Glu Ala Trp Arg Leu
50                  55                  60

Thr Asp Lys Thr Lys Ala Arg Tyr Gln Ser Lys Glu Asp Leu Glu Lys
65                  70                  75                  80

Ala Lys Lys Glu His Gly Ile Thr Tyr Gly Glu Trp Val Asn Asp Lys
                85                  90                  95

Val Ala Tyr Tyr His Asp Tyr Ser Lys Asp Gly Lys Thr Ala Val Asp
                100                 105                 110

Gln Glu His Gly Thr His Val Ser Gly Ile Leu Ser Gly Asn Ala Pro
               115                 120                 125

Ser Glu Thr Lys Glu Pro Tyr Arg Leu Glu Gly Ala Met Pro Glu Ala
130                135                  140

Gln Leu Leu Leu Met Arg Val Glu Ile Val Asn Gly Leu Ala Asp Tyr
145                150                  155                 160

Ala Arg Asn Tyr Ala Gln Ala Ile Arg Asp Ala Val Asn Leu Gly Ala
               165                 170                 175

Lys Val Ile Asn Met Ser Phe Gly Asn Ala Ala Leu Ala Tyr Ala Asn
               180                 185                 190

Leu Pro Asp Glu Thr Lys Lys Ala Phe Asp Tyr Ala Lys Ser Lys Gly
               195                 200                 205

Val Ser Ile Val Thr Ser Ala Gly Asn Asp Ser Ser Phe Gly Gly Lys
210                215                  220

Thr Arg Leu Pro Leu Ala Asp His Pro Asp Tyr Gly Val Val Gly Thr
225                230                  235                 240

Pro Ala Ala Ala Asp Ser Thr Leu Thr Val Ala Ser Tyr Ser Pro Asp
                245                 250                 255

Lys Gln Leu Thr Glu Thr Ala Thr Val Lys Thr Asp Asp His Gln Ala
                260                 265                 270

Lys Glu Met Pro Val Leu Ser Thr Asn Arg Phe Glu Pro Asn Lys Ala

```
            275                 280                 285
Tyr Asp Tyr Ala Tyr Asn Arg Gly Met Lys Glu Asp Asp Phe Lys
290                 295                 300

Asp Val Lys Gly Lys Ile Ala Leu Ile Glu Arg Gly Asp Ile Asp Phe
305                 310                 315                 320

Lys Asp Lys Ile Ala Asn Ala Lys Lys Ala Gly Ala Val Gly Val Leu
                    325                 330                 335

Ile Tyr Asp Asn Gln Asp Lys Gly Phe Pro Ile Glu Leu Pro Asn Val
            340                 345                 350

Asp Gln Met Pro Ala Ala Phe Ile Ser Arg Lys Asp Gly Leu Leu Leu
        355                 360                 365

Lys Asp Asn Ser Lys Lys Thr Ile Thr Phe Asn Ala Thr Pro Lys Val
370                 375                 380

Leu Pro Thr Ala Ser Asp Thr Lys Leu Ser Arg Phe Ser Ser Trp Gly
385                 390                 395                 400

Leu Thr Ala Asp Gly Asn Ile Lys Pro Asp Ile Ala Ala Pro Gly Gln
                    405                 410                 415

Asp Ile Leu Ser Ser Val Ala Asn Asn Lys Tyr Ala Lys Leu Ser Gly
            420                 425                 430

Thr Ser Met Ser Ala Pro Leu Val Ala Gly Ile Met Gly Leu Leu Gln
        435                 440                 445

Lys Gln Tyr Glu Thr Gln Tyr Pro Asp Met Thr Pro Ser Glu Arg Leu
450                 455                 460

Asp Leu Ala Lys Lys Val Leu Met Ser Ser Ala Thr Ala Leu Tyr Asp
465                 470                 475                 480

Glu Asp Glu Lys Ala Tyr Phe Ser Pro Arg Gln Gln Gly Ala Gly Ala
                    485                 490                 495

Val Asp Ala Lys Lys Ala Ser Ala Ala Thr Met Tyr Val Thr Asp Lys
            500                 505                 510

Asp Asn Thr Ser Ser Lys Val His Leu Asn Asn Val Ser Asp Lys Phe
        515                 520                 525

Glu Val Thr Val Thr Val His Asn Lys Ser Asp Lys Pro Gln Glu Leu
530                 535                 540

Tyr Tyr Gln Ala Thr Val Gln Thr Asp Lys Val Asp Gly Lys His Phe
545                 550                 555                 560

Ala Leu Ala Pro Lys Ala Leu Tyr Glu Thr Ser Trp Gln Lys Ile Thr
                    565                 570                 575

Ile Pro Ala Asn Ser Ser Lys Gln Val Thr Val Pro Ile Asp Ala Ser
            580                 585                 590

Arg Phe Ser Lys Asp Leu Leu Ala Gln Met Lys Asn Gly Tyr Phe Leu
        595                 600                 605

Glu Gly Phe Val Arg Phe Lys Gln Asp Pro Lys Lys Glu Glu Leu Met
610                 615                 620

Ser Ile Pro Tyr Ile Gly Phe Arg Gly Asp Phe Gly Asn Leu Ser Ala
625                 630                 635                 640

Leu Glu Lys Pro Ile Tyr Asp Ser Lys Asp Gly Ser Ser Tyr Tyr His
                    645                 650                 655

Glu Ala Asn Ser Asp Ala Lys Asp Gln Leu Asp Gly Asp Gly Leu Gln
            660                 665                 670

Phe Tyr Ala Leu Lys Asn Asn Phe Thr Ala Leu Thr Thr Glu Ser Asn
        675                 680                 685

Pro Trp Thr Ile Ile Lys Ala Val Lys Glu Gly Val Glu Asn Ile Glu
690                 695                 700
```

```
Asp Ile Glu Ser Ser Glu Ile Thr Glu Thr Ile Phe Ala Gly Thr Phe
705                 710                 715                 720

Ala Lys Gln Asp Asp Ser His Tyr Tyr Ile His Arg His Ala Asn
            725                 730                 735

Gly Lys Pro Tyr Ala Ala Ile Ser Pro Asn Gly Asp Gly Asn Arg Asp
                740                 745                 750

Tyr Val Gln Phe Gln Gly Thr Phe Leu Arg Asn Ala Lys Asn Leu Val
            755                 760                 765

Ala Glu Val Leu Asp Lys Glu Gly Asn Val Val Trp Thr Ser Glu Val
        770                 775                 780

Thr Glu Gln Val Val Lys Asn Tyr Asn Asn Asp Leu Ala Ser Thr Leu
785                 790                 795                 800

Gly Ser Thr Arg Phe Glu Lys Thr Arg Trp Asp Gly Lys Asp Lys Asp
                805                 810                 815

Gly Lys Val Val Val Asn Gly Thr Tyr Thr Tyr Arg Val Arg Tyr Thr
            820                 825                 830

Pro Ile Ser Ser Gly Ala Lys Glu Gln His Thr Asp Phe Asp Val Ile
        835                 840                 845

Val Asp Asn Thr Thr Pro Glu Val Ala Thr Ser Ala Thr Phe Ser Thr
    850                 855                 860

Glu Asp Arg Arg Leu Thr Leu Ala Ser Lys Pro Lys Thr Ser Gln Pro
865                 870                 875                 880

Ile Tyr Arg Glu Arg Ile Ala Tyr Thr Tyr Met Asp Glu Asp Leu Pro
                885                 890                 895

Thr Thr Glu Tyr Ile Ser Pro Asn Glu Asp Gly Thr Phe Thr Leu Pro
            900                 905                 910

Glu Glu Ala Glu Thr Met Glu Gly Thr Val Pro Leu Lys Met Ser
        915                 920                 925

Asp Phe Thr Tyr Val Val Glu Asp Met Ala Gly Asn Ile Thr Tyr Thr
            930                 935                 940

Pro Val Thr Lys Leu Leu Glu Gly His Ser
945                 950
```

<210> SEQ ID NO 5
<211> LENGTH: 943
<212> TYPE: PRT
<213> ORGANISM: Streptococcus pyogenes
<220> FEATURE:
<221> NAME/KEY: MISC_FEATURE
<222> LOCATION: (1)..(943)
<223> OTHER INFORMATION: ScpA protease variant

<400> SEQUENCE: 5

```
Lys Thr Ala Asp Thr Pro Ala Thr Ser Lys Ala Thr Ile Arg Asp Leu
1               5                   10                  15

Asn Asp Pro Ser Gln Val Lys Thr Leu Gln Glu Lys Ala Ser Lys Gly
            20                  25                  30

Ala Gly Thr Val Val Ala Val Ile Asp Ala Gly Phe Asp Lys Asn His
        35                  40                  45

Glu Ala Trp Arg Leu Thr Asp Lys Thr Lys Ala Arg Tyr Gln Ser Lys
    50                  55                  60

Glu Asp Leu Glu Lys Ala Lys Lys Glu His Gly Ile Thr Tyr Gly Glu
65                  70                  75                  80

Trp Val Asn Asp Lys Val Ala Tyr Tyr His Asp Tyr Ser Lys Asp Gly
                85                  90                  95
```

```
Lys Thr Ala Val Asp Gln Glu His Gly Thr His Val Ser Gly Ile Leu
                100                 105                 110
Ser Gly Asn Ala Pro Ser Glu Thr Lys Glu Pro Tyr Arg Leu Glu Gly
            115                 120                 125
Ala Met Pro Glu Ala Gln Leu Leu Met Arg Val Glu Ile Val Asn
        130                 135                 140
Gly Leu Ala Asp Tyr Ala Arg Asn Tyr Ala Gln Ala Ile Arg Asp Ala
145                 150                 155                 160
Val Asn Leu Gly Ala Lys Val Ile Asn Met Ser Phe Gly Asn Ala Ala
                165                 170                 175
Leu Ala Tyr Ala Asn Leu Pro Asp Glu Thr Lys Lys Ala Phe Asp Tyr
            180                 185                 190
Ala Lys Ser Lys Gly Val Ser Ile Val Thr Ser Ala Gly Asn Asp Ser
        195                 200                 205
Ser Phe Gly Gly Lys Thr Arg Leu Pro Leu Ala Asp His Pro Asp Tyr
    210                 215                 220
Gly Val Gly Thr Pro Ala Ala Asp Ser Thr Leu Thr Val Ala
225                 230                 235                 240
Ser Tyr Ser Pro Asp Lys Gln Leu Thr Glu Thr Ala Thr Val Lys Thr
                245                 250                 255
Asp Asp His Gln Ala Lys Glu Met Pro Val Leu Ser Thr Asn Arg Phe
            260                 265                 270
Glu Pro Asn Lys Ala Tyr Asp Tyr Ala Tyr Ala Asn Arg Gly Met Lys
        275                 280                 285
Glu Asp Asp Phe Lys Asp Val Lys Gly Lys Ile Ala Leu Ile Glu Arg
    290                 295                 300
Gly Asp Ile Asp Phe Lys Asp Lys Ile Ala Asn Ala Lys Lys Ala Gly
305                 310                 315                 320
Ala Val Gly Val Leu Ile Tyr Asp Asn Gln Asp Lys Gly Phe Pro Ile
                325                 330                 335
Glu Leu Pro Asn Val Asp Gln Met Pro Ala Ala Phe Ile Ser Arg Lys
            340                 345                 350
Asp Gly Leu Leu Leu Lys Asp Asn Ser Lys Lys Thr Ile Thr Phe Asn
        355                 360                 365
Ala Thr Pro Lys Val Leu Pro Thr Ala Ser Asp Thr Lys Leu Ser Arg
    370                 375                 380
Phe Ser Ser Trp Gly Leu Thr Ala Asp Gly Asn Ile Lys Pro Asp Ile
385                 390                 395                 400
Ala Ala Pro Gly Gln Asp Ile Leu Ser Ser Val Ala Asn Asn Lys Tyr
                405                 410                 415
Ala Lys Leu Ser Gly Thr Ser Met Ser Ala Pro Leu Val Ala Gly Ile
            420                 425                 430
Met Gly Leu Leu Gln Lys Gln Tyr Glu Thr Gln Tyr Pro Asp Met Thr
        435                 440                 445
Pro Ser Glu Arg Leu Asp Leu Ala Lys Lys Val Leu Met Ser Ser Ala
    450                 455                 460
Thr Ala Leu Tyr Asp Glu Asp Glu Lys Ala Tyr Phe Ser Pro Arg Gln
465                 470                 475                 480
Gln Gly Ala Gly Ala Val Asp Ala Lys Lys Ala Ser Ala Ala Thr Met
                485                 490                 495
Tyr Val Thr Asp Lys Asp Asn Thr Ser Ser Lys Val His Leu Asn Asn
            500                 505                 510
Val Ser Asp Lys Phe Glu Val Thr Val Thr Val His Asn Lys Ser Asp
```

```
                515                 520                 525
Lys Pro Gln Glu Leu Tyr Tyr Gln Ala Thr Val Gln Thr Asp Lys Val
530                 535                 540
Asp Gly Lys His Phe Ala Leu Ala Pro Lys Ala Leu Tyr Glu Thr Ser
545                 550                 555                 560
Trp Gln Lys Ile Thr Ile Pro Ala Asn Ser Ser Lys Gln Val Thr Val
                565                 570                 575
Pro Ile Asp Ala Ser Arg Phe Ser Lys Asp Leu Leu Ala Gln Met Lys
                580                 585                 590
Asn Gly Tyr Phe Leu Glu Gly Phe Val Arg Phe Lys Gln Asp Pro Lys
                595                 600                 605
Lys Glu Glu Leu Met Ser Ile Pro Tyr Ile Gly Phe Arg Gly Asp Phe
610                 615                 620
Gly Asn Leu Ser Ala Leu Glu Lys Pro Ile Tyr Asp Ser Lys Asp Gly
625                 630                 635                 640
Ser Ser Tyr Tyr His Glu Ala Asn Ser Asp Ala Lys Asp Gln Leu Asp
                645                 650                 655
Gly Asp Gly Leu Gln Phe Tyr Ala Leu Lys Asn Asn Phe Thr Ala Leu
                660                 665                 670
Thr Thr Glu Ser Asn Pro Trp Thr Ile Ile Lys Ala Val Lys Glu Gly
                675                 680                 685
Val Glu Asn Ile Glu Asp Ile Glu Ser Ser Gly Ile Thr Glu Thr Ile
690                 695                 700
Phe Ala Gly Thr Phe Ala Lys Gln Asp Asp Asp Ser His Tyr Tyr Ile
705                 710                 715                 720
His Arg His Ala Asn Gly Lys Pro Tyr Ala Ala Ile Ser Pro Asn Gly
                725                 730                 735
Asp Gly Asn Arg Asp Tyr Val Gln Phe Gln Gly Thr Phe Leu Arg Asn
                740                 745                 750
Ala Lys Asn Leu Val Ala Glu Val Leu Asp Lys Glu Gly Asn Val Val
                755                 760                 765
Trp Thr Ser Glu Val Thr Glu Gln Val Val Lys Asn Tyr Asn Asn Asp
                770                 775                 780
Leu Ala Ser Thr Leu Gly Ser Thr Arg Phe Glu Lys Thr Arg Trp Asp
785                 790                 795                 800
Gly Lys Asp Lys Asp Gly Lys Val Val Asn Gly Thr Tyr Thr Tyr
                805                 810                 815
Arg Val Arg Tyr Thr Pro Ile Ser Ser Gly Ala Lys Glu Gln His Thr
                820                 825                 830
Asp Phe Asp Val Ile Val Asp Asn Thr Thr Pro Glu Val Ala Thr Ser
                835                 840                 845
Ala Thr Phe Ser Thr Glu Asp Arg Arg Leu Thr Leu Ala Ser Lys Pro
850                 855                 860
Lys Thr Ser Gln Pro Ile Tyr Arg Glu Arg Ile Ala Tyr Thr Tyr Met
865                 870                 875                 880
Asp Glu Asp Leu Pro Thr Thr Glu Tyr Ile Ser Pro Asn Glu Asp Gly
                885                 890                 895
Thr Phe Thr Leu Pro Glu Glu Ala Glu Thr Met Glu Gly Gly Thr Val
                900                 905                 910
Pro Leu Lys Met Ser Asp Phe Thr Tyr Val Val Glu Asp Met Ala Gly
                915                 920                 925
Asn Ile Thr Tyr Thr Pro Val Thr Lys Leu Leu Glu Gly His Ser
                930                 935                 940
```

```
<210> SEQ ID NO 6
<211> LENGTH: 74
<212> TYPE: PRT
<213> ORGANISM: Homo sapiens
<220> FEATURE:
<221> NAME/KEY: MISC_FEATURE
<222> LOCATION: (1)..(74)
<223> OTHER INFORMATION: Human C5a protein

<400> SEQUENCE: 6

Met Leu Gln Lys Lys Ile Glu Glu Ile Ala Ala Lys Tyr Lys His Ser
1               5                   10                  15

Val Val Lys Lys Cys Cys Tyr Asp Gly Ala Cys Val Asn Asn Asp Glu
            20                  25                  30

Thr Cys Glu Gln Arg Ala Ala Arg Ile Ser Leu Gly Pro Arg Cys Ile
        35                  40                  45

Lys Ala Phe Thr Glu Cys Cys Val Val Ala Ser Gln Leu Arg Ala Asn
    50                  55                  60

Ile Ser His Lys Asp Met Gln Leu Gly Arg
65                  70
```

APPARATUS FOR THE EXTRACORPOREAL TREATMENT OF BLOOD

CROSS-REFERENCE TO RELATED APPLICATIONS

This application claims priority from European Patent Application No. 13197790.2, filed on Dec. 17, 2013, the contents of this application are hereby incorporated by reference in its entirety.

BACKGROUND OF THE INVENTION

State-of-the-art hospital treatment for sepsis is the implementation of 'The Sepsis Six' (PMID 21398303). These are a series of interventions to stabilize the patient, including delivery of antibiotics, microbial culture, delivery of high-flow oxygen, and fluids. To date, interventions to mitigate organ damage in sepsis have failed. Treatment with Drotrecogin alfa activated, a serine protease involved in switching off coagulation, was, until very recently, the major FDA-approved intervention for treatment of human sepsis. However in 2011 FDA announcing that Eli Lilly had withdrawn Xigris (Drotrecogin alfa). On the 8 Aug. 2012, AstraZeneca announced that a Phase IIb study testing the efficacy of Cyto-Fab™, an anti-TNFα, polyclonal antibody fragment, for treatment of severe sepsis and/or septic shock, did not show any significant improvement over placebo and AZ halted any further developments.

Two additional treatments have been proposed based on a blood purification strategy with some similarity to that proposed in this document. Cytosorb's IL-8 adsorption cassette is based on a porous material that adsorbs the cytokine IL-8, but the technique is non-selective, and removes other small protein components of the blood (found on the world wide web at cytosorbents.com/tech.htm). The second strategy is a specific adsorption resin removing bacterial LPS from blood circulated through a cassette (found on the world wide web at altecomedical.com/market_product.php), and is a treatment limited to sepsis caused by Gram negative bacteria.

There is a large body of evidence establishing the role of C5a is sepsis. The Cell Envelope Protease ScpA targets the immune proinflammatory mediator C5a and specifically cleaves the mediator rendering it active.

It is an object of the invention to overcome at least one of the above-referenced problems.

SUMMARY OF THE INVENTION

The invention is based on a method and device for the extracorporeal treatment of inflammatory conditions in a patient, especially auto-immune diseases, sepsis or septicemia, that involves reacting blood that has been removed from a patient with a protease enzyme immobilized to a support in which the enzyme is specific for a pro-inflammatory mediator present in the blood of the patient and is capable of cleaving the pro-inflammatory mediator and thereby reducing the abundance of pro-inflammatory mediator in the blood of the patient prior to the return of the treated blood to the patient.

In a first aspect, the invention relates to an apparatus for the extracorporeal treatment of blood comprising:
  an extracorporeal blood circuit;
  optionally, a pump configured to provide fluid displacement within the extracorporeal blood circuit; and
  a reaction chamber connected to the extracorporeal blood circuit and configured to receive blood or a pro-inflammatory mediator containing blood fraction from the circuit and treat the blood or pro-inflammatory mediator containing blood fraction,
characterized in that the reaction chamber comprises a protease enzyme irreversibly immobilized to a support, in which the protease enzyme is specific for, and capable of irreversibly cleaving, a human pro-inflammatory mediator present in the blood or plasma such that the chemoattractant capability of the pro-inflammatory mediator is reduced or preferably abrogated, wherein the abundance of functional pro-inflammatory mediator in the treated blood or plasma is less than that in the untreated blood or plasma.

Compared with extracorporeal treatment devices that operate on the basis of adsorption of pro-inflammatory mediators, the apparatus of the invention has a number of advantages. Each molecule of enzyme can cleave a large number of molecules of substrate during a treatment operation; this contrasts with the adsorption process in which the ligand, once bound to its target molecule, is unavailable for binding with further target molecules. Second, the affinity antibody-based approaches of the prior art are susceptible to cross-reacting with non-target molecules, and involve significant costs in the development and generation of suitable antibodies. In contracts, enzymes that are specific to pro-inflammatory mediators are known from the literature, and can be easily produced using recombinant DNA technology.

Preferably, the pro-inflammatory mediator is selected from a group consisting of, but not limited to: C3a, C4a, C5a, IL-8, IL-6, TNFα, IL-1, or Mig. Thus, in one embodiment, the protease enzyme is capable of cleaving a human pro-inflammatory mediator selected from a group consisting of, but not limited to, C3a, C4a, C5a, IL-8, IL-6, TNFα, IL-1, and Mig.

In a preferred embodiment, the invention provides an apparatus for the extracorporeal treatment of blood comprising:
  an extracorporeal blood circuit;
  optionally, a pump configured to provide fluid displacement within the extracorporeal blood circuit; and
  a reaction chamber connected to the extracorporeal blood circuit and configured to receive blood or a human C5a-containing blood fraction from the circuit and treat the blood or human C5a-containing blood fraction,
characterized in that the reaction chamber comprises a protease enzyme irreversibly immobilized to a support, in which the protease enzyme is specific for, and capable of irreversibly cleaving, human C5a present in the blood or blood fraction such that the chemoattractant capability of the cleaved human C5a is reduced, wherein the abundance of the functional human C5a in the treated blood or blood fraction is less than that in the untreated blood or blood fraction.

As used herein, the term "functional human C5a" should be understood to mean human C5a having chemoattractant capability as determined using the chemoattractant capability assay described below. Likewise, the term "non-functional human C5a" should be understood to mean cleaved C5a protein that has reduced, or is devoid of, chemoattractant capability as determined using the chemoattractant capability assay described below.

The invention also provides an apparatus for treating human blood or a pro-inflammatory mediator-containing blood fraction, the apparatus comprising a protease enzyme irreversibly bound to a support, in which the protease enzyme is specific for, and capable of irreversibly cleaving, a pro-inflammatory mediator present in the blood or blood fraction such that the chemoattractant capability of the cleaved human pro-inflammatory mediator is reduced.

The invention also provides an apparatus for treating human blood or a C5a-containing blood fraction, the apparatus comprising a protease enzyme irreversibly bound to a support, in which the protease enzyme is specific for, and capable of irreversibly cleaving, human C5a present in the blood or blood fraction such that the chemoattractant capability of the cleaved human C5a is reduced.

The invention also provides a protease enzyme comprising the sequence of A-B-C-D, in which:

A is a protease enzyme that is specific for, and capable of irreversibly cleaving, a human pro-inflammatory mediator present in the blood such that the chemoattractant capability of the cleaved pro-inflammatory mediator is reduced, B is a poly-lysine, poly-cysteine or poly-glutamate motif, C is a spacer (for example a short peptide of 2 to 20 amino acids), and D is a poly-histidine motif.

Preferably, the protease enzyme is a recombinant bacterial C5a protease comprising a sequence of SEQUENCE ID NO: 3 or a functional variant thereof, typically having at least 70%, 80% or 90% sequence identity with SEQUENCE ID NO: 3.

The term "functional variant" as applied to SEQUENCE ID NO: 3 means a protease that is specific for, and capable of irreversibly cleaving, human C5a such that the chemoattractant capability of the cleaved human C5a is reduced, or preferably abrogated.

Examples functional variants of SEQUENCE ID NO: 3 are selected from SEQUENCE ID NO: 4 and SEQUENCE ID NO:5.

In one embodiment, the apparatus of the invention includes separating means adapted to separate the blood into a C5a-containing fraction and a non-05a containing fraction, wherein the reaction chamber receives the C5a-containing fraction. The separating means could be, for example, a filter configured to separate the blood or a fraction thereof into a low-molecular weight containing fraction and a second fraction, wherein the low molecular weight containing fraction is the C5a containing fraction.

Suitably, the apparatus of the invention includes means configured to recombine the treated C5a-containing fraction (i.e. the low molecular weight fraction) with the second non-05a containing fraction. The recombined fractions are then returned to the patient.

In one preferred embodiment of the invention, a C-terminal of the protease enzyme comprises a first tag and a second tag located distally of the first tag and separated from the first tag by a spacer. Typically, the support comprises a coordinated transition metal ion and one or more functional groups. Suitably, the first tag comprises a motif capable of covalently reacting with the one or more functional groups, and wherein the second tag comprises a motif capable of interacting with the coordinated transition metal ion. In this manner, the protease enzyme can be oriented with respect to the surface such that the C-terminus of the enzyme is disposed adjacent to the surface (this is achieved by the interaction between the second tag and the coordinated transition metal of the support surface), thus allowing the adjacent first tag to covalently bind to the functional groups on the surface. This will prevent unspecific binding between functional groups on the surface and lysine residues in the protease enzyme.

Preferably, the first tag is selected from poly-lysine, poly-glutamate, or poly-cysteine tag, and the functional groups on the surface are groups that are capable of covalently binding with these motifs.

Suitably, the second tag comprises a poly-histidine tag or another tag capable of interaction with a transition metal.

Preferably, the coordinated transition metal ion is selected from $Ni^{2+}$, $Co^{2+}$, $Zn^{2+}$, and $Cu^{2+}$.

Both tags can be appended onto the DNA sequence by PCR based methods using an oligonucleotide synthesized to contain the required sequence.

Typically, the support comprises a silica material, preferably a mesoporous silica material, preferably modified monodispersed mesoporous silicate material, and ideally a $Ni^{2+}$-modified mesoporous silica material. Other potential materials for the support include but are not limited to methacrylates, polyacrylamides, polypyrroles and polysaccharides.

Suitably, the support comprises a bead. Preferably, the reaction chamber comprises a column containing a multiplicity of beads.

The invention also relates to an apparatus of the invention for use in a method for the ex-vivo treatment of blood in a mammal, typically a human. Preferably, the mammal has an inflammatory condition such as sepsis.

The nucleic acid sequence encoding the bacterial C5a protease, ScpA from *Streptococcus pyogenes*, is provided in SEQUENCE ID NO: 1 below:

```
DNA sequence
                                        (SEQUENCE ID NO: 1)
GGATCCAATACTGTGACAGAAGACACTCCTGCTACCGAACAAGCCGTAGA

AACCCCACAACCAACAGCGGTTTCTGAGGAAGCACCATCATCATCAAAGG

AAACCAAAATCCCACAAACTCCTGGTGATGCAGAAGAAACAGTAGCAGAT

GACGCTAATGATCTAGCCCCTCAAGCTCCTGCTAAAACTGCTGATACACC

AGCAACCTCAAAAGCGACTATTAGGGATTTGAACGACCCTTCTCAGGTCA

AAACCCTGCAGGAAAAAGCAGGCAAGGGAGCTGGGACTGTTGTTGCAGTG

ATTGATGCTGGTTTTGATAAAAATCATGAAGCGTGGCGCTTAACAGACAA

AACTAAAGCACGTTACCAATCAAAAGAAGATCTTGAAAAAGCTAAAAAAG

AGCACGGTATTACCTATGGCGAGTGGGTCAATGATAAGGTTGCTTATTAC

CACGATTATAGTAAAGATGGTAAAACCGCTGTCGATCAAGAGCACGGCAC

ACACGTGTCAGGGATCTTGTCAGGAAATGCTCCATCTGAAACGAAAGAAC

CTTACCGCCTAGAAGGTGCGATGCCTGAGGCTCAATTGCTTTTGATGCGT

GTCGAAATTGTAAATGGACTAGCAGACTATGCTCGTAACTACGCTCAAGC

TATCAGAGATGCTGTCAACTTGGGAGCTAAGGTGATTAATATGAGCTTTG

GTAATGCTGCACTAGCTTACGCCAACCTTCCAGACGAAACCAAAAAAGCC

TTTGACTATGCCAAATCAAAAGGTGTTAGCATTGTGACCTCAGCTGGTAA

TGATAGTAGCTTTGGGGGCAAAACCCGTCTACCTCTAGCAGATCATCCTG

ATTATGGGGTGGTTGGGACGCCTGCAGCGGCAGACTCAACATTGACAGTT

GCTTCTTACAGCCCAGATAAACAGCTCACTGAAACTGCTACGGTCAAAAC

AGACGATCATCAAGCTAAAGAAATGCCTGTTCTTTCAACAAACCGTTTTG

AGCCAAACAAGGCTTACGACTATGCTTATGCTAATCGTGGGATGAAAGAA

GATGATTTTAAGGATGTCAAAGGCAAAATTGCCCTTATTGAACGTGGTGA

TATTGATTTCAAAGATAAGATTGCAAACGCTAAAAAAGCTGGTGCTGTAG

GGGTCTTGATCTATGACAATCAAGACAAGGGCTTCCCGATTGAATTGCCA

AATGTTGATCAGATGCCTGCGGCCTTTATCAGTCGAAAAGACGGTCTCTT

ATTAAAAGACAATTCTAAAAAAACCATCACCTTCAATGCGACACCTAAGG

TATTGCCAACAGCAAGTGACACCAAACTAAGCCGCTTCTCAAGCTGGGGT
```

-continued

```
TTGACAGCTGACGGCAATATTAAGCCAGATATTGCAGCACCCGGCCAAGA

TATTTTGTCATCAGTGGCTAACAACAAGTATGCCAAACTTTCTGGAACTA

GTATGTCTGCGCCATTGGTAGCGGGTATCATGGGACTATTGCAAAAGCAA

TATGAGACACAGTATCCTGATATGACACCATCAGAGCGTCTTGATTTAGC

TAAAAAAGTATTGATGAGCTCAGCAACTGCCTTATATGATGAAGATGAAA
AAGCTTATTTTTCTCCTCGCCAACAAGGAGCAGGAGCAGTCGATGCTAAA
AAAGCTTCAGCAGCAACGATGTATGTGACAGATAAGGACAATACCTCAAG

CAAGGTTCACCTGAACAATGTTTCTGATAAATTTGAAGTAACAGTAACAG

TTCACAACAAATCTGATAAACCTCAAGAGTTGTATTACCAAGCAACTGTT

CAAACAGATAAAGTAGATGGAAAACACTTTGCCTTGGCTCCTAAAGCATT

GTATGAGACATCATGGCAAAAAATCACAATTCCAGCCAATAGCAGCAAAC

AAGTCACCGTTCCAATCGATGCTAGTCGATTTAGCAAGGACTTGCTTGCC

CAAATGAAAAATGGCTATTTCTTAGAAGGTTTTGTTCGTTTCAAACAAGA

TCCTAAAAAAGAAGAGCTTATGAGCATTCCATATATTGGTTTCCGAGGTG

ATTTTGGCAATCTGTCAGCCTTAGAAAAACCAATCTATGATAGCAAAGAC

GGTAGCAGCTACTATCATGAAGCAAATAGTGATGCCAAAGACCAATTAGA

TGGTGATGGATTACAGTTTTACGCTCTGAAAAATAACTTTACAGCACTTA

CCACAGAGTCTAACCCATGGACGATTATTAAAGCTGTCAAAGAAGGGGTT

GAAAACATAGAGGATATCGAATCTTCAGAGATCACAGAAACCATTTTTGC

AGGTACTTTTGCAAAACAAGACGATGATAGCCACTACTATATCCACCGTC

ACGCTAATGGCAAACCATATGCTGCGATCTCTCCAAATGGGGACGGTAAC

AGAGATTATGTCCAATTCCAAGGTACTTTCTTGCGTAATGCTAAAAACCT

TGTGGCTGAAGTCTTGGACAAAGAAGGAAATGTTGTTTGGACAAGTGAGG

TAACCGAGCAAGTTGTTAAAAACTACAACAATGACTTGGCAAGCACACTT

GGTTCAACCCGTTTTGAAAAAACGCGTTGGGACGGTAAAGATAAAGACGG

CAAAGTTGTTGTTAACGGAACCTACACCTATCGTGTCCGCTACACTCCGA

TTAGCTCAGGTGCAAAAGAACAACACACTGATTTTGATGTGATTGTAGAC

AATACGACACCTGAAGTCGCAACATCGGCAACATTCTCAACAGAAGATCG

TCGTTTGACACTTGCATCTAAACCAAAAACCAGCCAACCGATTTACCGTG

AGCGTATTGCTTACACTTATATGGATGAGGATCTGCCAACAACAGAGTAT

ATTTCTCCAAATGAAGATGGTACCTTTACTCTTCCTGAAGAGGCTGAAAC

AATGGAAGGCGGTACTGTTCCATTGAAAATGTCAGACTTTACTTATGTTG

TTGAAGATATGGCTGGTAACATCACTTATACACCAGTGACTAAGCTATTG

GAGGGCCACTCTTAA
```

The amino acid sequence of the bacterial C5a pro-protease, ScpA from *Streptococcus pyogenes*, is provided in SEQUENCE ID NO: 2 below:

```
Protein sequence
                                        (SEQUENCE ID NO: 2)
GPLGSNTVTEDTPATEQAVETPQPTAVSEEAPSSSKETKIPQTPGDAEET
VADDANDLAPQAPAKTADTPATSKATIRDLNDPSQVKTLQEKASKGAGTV
```

-continued

```
VAVIDAGFDKNHEAWRLTDKTKARYQSKEDLEKAKKEHGITYGEWVNDKV
AYYHDYSKDGKTAVDQEHGTHVSGILSGNAPSETKEPYRLEGAMPEAQLL
LMRVEIVNGLADYARNYAQAIRDAVNLGAKVINMSFGNAALAYANLPDET
KKAFDYAKSKGVSIVTSAGNDSSFGGKTRLPLADHPDYGVVGTPAAADST
LTVASYSPDKQLTETATVKTDDHQAKEMPVLSTNRFEPNKAYDYAYANRG
MKEDDFKDVKGKIALIERGDIDFKDKIANAKKAGAVGVLIYDNQDKGFPI
ELPNVDQMPAAFISRKDGLLLKDNSKKTITFNATPKVLPTASDTKLSRFS
SWGLTADGNIKPDIAAPGQDILSSVANNKYAKLSGTSMSAPLVAGIMGLL
QKQYETQYPDMTPSERLDLAKKVLMSSATALYDEDEKAYFSPRQQGAGAV
DAKKASAATMYVTDKDNTSSKVHLNNVSDKFEVTVTVHNKSDKPQELYYQ
ATVQTDKVDGKHFALAPKALYETSWQKITIPANSSKQVTVPIDASRFSKD
LLAQMKNGYFLEGFVRFKQDPKKEELMSIPYIGFRGDFGNLSALEKPIYD
SKDGSSYYHEANSDAKDQLDGDGLQFYALKNNFTALTTESNPWTIIKAVK
EGVENIEDIESSEITETIFAGTFAKQDDDSHYYIHRHANGKPYAAISPNG
DGNRDYVQFQGTFLRNAKNLVAEVLDKEGNVVWTSEVTEQVVKNYNNDLA
STLGSTRFEKTRWDGKDKDGKVVVNGTYTYRVRYTPISSGAKEQHTDFDV
IVDNTTPEVATSATFSTEDRRLTLASKPKTSQPIYRERIAYTYMDEDLPT
TEYISPNEDGTFTLPEEAETMEGGTVPLKMSDFTYVVEDMAGNITYTPVT
KLLEGHS
```

The amino acid sequence of mature bacterial C5a protease, ScpA from *Streptococcus pyogenes*, is provided in SEQUENCE ID NO: 3 below:

```
AEETVADDANDLAPQAPAKTADTPATSKATIRDLNDPSQVKTLQEKASKG
AGTVVAVIDAGEDKNHEAWRLTDKTKARYQSKEDLEKAKKEHGITYGEWV
NDKVAYYHDYSKDGKTAVDQEHGTHVSGILSGNAPSETKEPYRLEGAMPE
AQLLLMRVEIVNGLADYARNYAQAIRDAVNLGAKVINMSEGNAALAYANL
PDETKKAFDYAKSKGVSIVTSAGNDSSFGGKTRLPLADHPDYGVVGTPAA
ADSTLTVASYSPDKQLTETATVKTDDHQAKEMPVLSTNRFEPNKAYDYAY
ANRGMKEDDEKDVKGKIALIERGDIDEKDKIANAKKAGAVGVLIYDNQDK
GFPIELPNVDQMPAAFISRKDGLLLKDNSKKTITFNATPKVLPTASDTKL
SRFSSWGLTADGNIKPDIAAPGQDILSSVANNKYAKLSGTSMSAPLVAGI
MGLLQKQYETQYPDMTPSERLDLAKKVLMSSATALYDEDEKAYFSPRQQG
AGAVDAKKASAATMYVTDKDNTSSKVHLNNVSDKFEVTVTVHNKSDKPQE
LYYQATVQTDKVDGKHFALAPKALYETSWQKITIPANSSKQVTVPIDASR
FSKDLLAQMKNGYFLEGFVREKQDPKKEELMSIPYIGFRGDFGNLSALEK
PIYDSKDGSSYYHEANSDAKDQLDGDGLQFYALKNNFTALTTESNPWTII
KAVKEGVENIEDIESSEITETIFAGTFAKQDDDSHYYIHRHANGKPYAAI
SPNGDGNRDYVQFQGTFLRNAKNLVAEVLDKEGNVVWTSEVTEQVVKNYN
NDLASTLGSTRFEKTRWDGKDKDGKVVVNGTYTYRVRYTPISSGAKEQHT
```

-continued
DFDVIVDNTTPEVATSATESTEDRRLTLASKPKTSQPIYRERIAYTYMDE

DLPTTEYISPNEDGTFTLPEEAETMEGGTVPLKMSDFTYVVEDMAGNITY

TPVTKLLEGHS

The amino acid sequence of a first variant of mature bacterial C5a protease, ScpA from Streptococcus pyogenes, is provided in SEQUENCE ID NO: 4 below:

DANDLAPQAPAKTADTPATSKATIRDLNDPSQVKTLQEKASKGAGTVVAV

IDAGFDKNHEAWRLTDKTKARYQSKEDLEKAKKEHGITYGEWVNDKVAYY

HDYSKDGKTAVDQEHGTHVSGILSGNAPSETKEPYRLEGAMPEAQLLLMR

VEIVNGLADYARNYAQAIRDAVNLGAKVINMSFGNAALAYANLPDETKKA

FDYAKSKGVSIVTSAGNDSSFGGKTRLPLADHPDYGVVGTPAAADSTLTV

ASYSPDKQLTETATVKTDDHQAKEMPVLSTNRFEPNKAYDYAYANRGMKE

DDFKDVKGKIALIERGDIDFKDKIANAKKAGAVGVLIYDNQDKGFPIELP

NVDQMPAAFISRKDGLLLKDNSKKTITFNATPKVLPTASDTKLSRFSSWG

LTADGNIKPDIAAPGQDILSSVANNKYAKLSGTSMSAPLVAGIMGLLQKQ

YETQYPDMTPSERLDLAKKVLMSSATALYDEDEKAYFSPRQQGAGAVDAK

KASAATMYVTDKDNTSSKVHLNNVSDKFEVTVTVHNKSDKPQELYYQATV

QTDKVDGKHFALAPKALYETSWQKITIPANSSKQVTVPIDASRFSKDLLA

QMKNGYFLEGFVRFKQDPKKEELMSIPYIGFRGDFGNLSALEKPIYDSKD

GSSYYHEANSDAKDQLDGDGLQFYALKNNFTALTTESNPWTIIKAVKEGV

ENIEDIESSEITETIFAGTFAKQDDDSHYYIHRHANGKPYAAISPNGDGN

RDYVQFQGTFLRNAKNLVAEVLDKEGNVVWTSEVTEQVVKNYNNDLASTL

GSTRFEKTRWDGKDKDGKVVVNGTYTYRVRYTPISSGAKEQHTDFDVIVD

NTTPEVATSATFSTEDRRLTLASKPKTSQPIYRERIAYTYMDEDLPTTEY

ISPNEDGTFTLPEEAETMEGGTVPLKMSDFTYVVEDMAGNITYTPVTKLL

EGHS

The amino acid sequence of a second variant of mature bacterial C5a protease, ScpA from *Streptococcus pyogenes*, is provided in SEQUENCE ID NO: 5 below:

KTADTPATSKATIRDLNDPSQVKTLQEKASKGAGTVVAVIDAGFDKNHEA

WRLTDKTKARYQSKEDLEKAKKEHGITYGEWVNDKVAYYHDYSKDGKTAV

DQEHGTHVSGILSGNAPSETKEPYRLEGAMPEAQLLLMRVEIVNGLADYA

RNYAQAIRDAVNLGAKVINMSFGNAALAYANLPDETKKAFDYAKSKGVSI

VTSAGNDSSFGGKTRLPLADHPDYGVVGTPAAADSTLTVASYSPDKQLTE

TATVKTDDHQAKEMPVLSTNRFEPNKAYDYAYANRGMKEDDFKDVKGKIA

LIERGDIDFKDKIANAKKAGAVGVLIYDNQDKGFPIELPNVDQMPAAFIS

RKDGLLLKDNSKKTITFNATPKVLPTASDTKLSRFSSWGLTADGNIKPDI

AAPGQDILSSVANNKYAKLSGTSMSAPLVAGIMGLLQKQYETQYPDMTPS

ERLDLAKKVLMSSATALYDEDEKAYFSPRQQGAGAVDAKKASAATMYVTD

KDNTSSKVHLNNVSDKFEVTVTVHNKSDKPQELYYQATVQTDKVDGKHFA

LAPKALYETSWQKITIPANSSKQVTVPIDASRFSKDLLAQMKNGYFLEGF

-continued

VRFKQDPKKEELMSIPYIGFRGDFGNLSALEKPIYDSKDGSSYYHEANSD

AKDQLDGDGLQFYALKNNFTALTTESNPWTIIKAVKEGVENIEDIESSEI

TETIFAGTFAKQDDDSHYYIHRHANGKPYAAISPNGDGNRDYVQFQGTFL

RNAKNLVAEVLDKEGNVVWTSEVTEQVVKNYNNDLASTLGSTRFEKTRWD

GKDKDGKVVVNGTYTYRVRYTPISSGAKEQHTDFDVIVDNTTPEVATSAT

FSTEDRRLTLASKPKTSQPIYRERIAYTYMDEDLPTTEYISPNEDGTFTL

EPEAETMEGGTVPLKMSDFTYVVEDMAGNITYTPVTKLLEGHS

The proteases of SEQUENCE ID NO:s 2, 3, 4 and 5 are all capable of cleaving human C5a such that the chemoattractant capability of the cleaved protease is abrogated.

The amino acid sequence of C5a protein is provided in SEQUENCE ID NO: 6 below.

C5a protein (SEQUENCE ID NO: 6)

MLQKKIEEIAAKYKHSVVKKCCYDGACVNNDETCEQRAARISLGPRCIKA

FTECCVVASQLRANISHKDMQLGR

Other proteases that are specific to, and capable of cleaving, human C5a include ScpB from *Streptococcus agalactiae*, and functional variants thereof (Brown et al). Examples of protease enzymes capable of specifically cleaving IL-8 include ScpC from *Streptococcus pyogenes*, SpyCEP from *Streptococcus agalactiae* and functional variants thereof (Fritzer et al, Kaur et al, Zinkernagel et al, Sjolinder et al, and Hidalgo et al)

Examples of protease enzymes capable of specifically cleaving IL-6 include a published *Pseudomonas* enzyme which degrades it completely (Matheson et al). Also gingipains K and R seem to have degrading activity against several mediators, but lack specificity required.

Suitably, the apparatus further comprising means of separating whole blood into a plasma fraction and a cellular fraction, and means for recombining the cellular fraction with the treated plasma fraction. In a separation process, the plasma in the patient's blood is typically segregated from its remaining constituents. The separated plasma is mixed with an acetate buffer saturated with heparin. This lowers the plasma's degree of acidity (pH value) to 5.12, causing the LDL cholesterol, Lp(a) and fibrinogen to drop selectively out of the plasma. Together with the heparin additive, the separated constituents form insoluble precipitates which can be removed from the plasma in a single filtration stage. Unused surplus heparin is held back in a separate adsorber, and bicarbonate ultrafiltration is used to restore the purified plasma to the physiologically acceptable level. The selectively treated, purified plasma is then remixed with the remaining blood constituents and supplied back to the patient. During H.E.L.P. apheresis, these four steps (plasma separation, precipitation with subsequent filtration, heparin adsorption and ultrafiltration) are performed by a single device, the PLASMAT Futura. Examples of devices capable of separating whole blood into a plasma fraction and a cellular fraction in extracorporeal blood circuits are known to the person skilled in the art, and include plasmaphoresis equipment (for example B Braun PLASMAT Futura) and hemodialysis equipment (for example Gambro PHEONIX found on the world wide web at gambro.com/en/global/Products/Hemodialysis/Monitors/Phoenix-dialysis-system/)

Typically, the reaction chamber comprises a column comprising beads in which the enzyme is immobilized to the beads. Alternatively, the reaction chamber may comprise a cartridge.

In a further aspect, the invention relates to a method for the treatment or prevention of an inflammatory condition in a human comprising the steps of reacting blood that has been removed from the patient, or a pro-inflammatory mediator containing fraction of the blood, with a protease enzyme immobilized to a support, in which the protease enzyme is specific for, and capable of irreversibly cleaving, a human pro-inflammatory mediator present in the blood or fraction such that the chemoattractant capability of the pro-inflammatory mediator is reduced or preferably abrogated, wherein the abundance of functional pro-inflammatory mediator in the treated blood or fraction is less than that in the untreated blood or fraction.

Typically, the human pro-inflammatory mediator is selected from the group consisting of, but not limited to, C3a, C4a, C5a, IL-8, IL-6, TNFα, IL-1, and Mig.

In a further aspect, the invention relates to a method for the treatment or prevention of an inflammatory condition in a human comprising the steps of reacting blood that has been removed from the patient, or a pro-inflammatory mediator containing fraction of the blood, with a protease enzyme immobilized to a support, in which the protease enzyme is specific for, and capable of irreversibly cleaving, human C5a present in the blood or fraction such that the chemoattractant capability of the cleaved human C5a is reduced or preferably abrogated, wherein the abundance of functional C5a in the treated blood or fraction is less than that in the untreated blood or plasma.

Suitably, the method includes the steps of separating the blood into a plasma fraction and a cellular fraction, treating the plasma fraction, and then recombining the cellular fraction with the treated plasma fraction prior to returning the blood to the patient.

Alternatively, or in addition, the method includes the steps of separating the blood into a C5a containing fraction (for example, a low molecular weight fraction) fraction and a second fraction, treating the C5a containing fraction, and then recombining the second fraction with the treated C5a containing fraction prior to returning the blood to the patient.

Typically, the method is carried out in a continuous fashion using an extracorporeal blood circuit.

Suitably, the protease enzyme is a recombinant protein.

The invention also relates to support and a recombinant protease enzyme immobilized to the support, in which the recombinant protease enzyme comprises a C-terminal poly-histidine tag and a C-terminal poly-lysine tag, and in which the recombinant protease enzyme comprises a protease that is specific for, and capable of irreversibly cleaving, a human pro-inflammatory mediator present in the blood or plasma.

In this specification, the term "extracorporeal blood circuit" should be understood to mean an arrangement of conduits capable of removing blood from the body for treatment outside of the body and returning the thus treated blood to the body.

In this specification, the term "reaction chamber" should be understood to mean a chamber adapted to receive blood or plasma from the extracorporeal blood circuit and allow contact between the blood or plasma and protease enzyme that is immobilized to a support within the reaction chamber.

In this specification, the term "plasma" should be understood to mean blood from which cells have been fully or partially removed.

In this specification, the term "pro-inflammatory mediator" should be understood to mean a host proteinaceous entity produced in the auto-immune or sepsis response which stimulates other components of the host immune system, in particular causing migration or stimulation of leukocytes of any class and progenitor forms of these cells. Specific examples of pro-inflammatory mediators specific to the human inflammatory response include C3a, C4a, C5a, IL-8, IL-6, TNFα, IL-1, and Mig.

In the specification, the term "protease enzyme that is specific for a human pro-inflammatory mediator" should be understood to mean an enzyme with the capacity to selectively, or ideally solely, break peptide bonds of pro-inflammatory mediators of human origin by hydrolysis. The protease may also be derived from the parent protease, and modified to include a functionalization group, for example one or more of a poly-histidine, poly-lysine, or poly-glutamic acid tag.

In this specification, the term "functional variant thereof" as applied to a specific protease enzyme should be understood to mean a variant of the protease enzyme that retains the ability to specifically bind and irreversibly cleave the target pro-inflammatory mediator such that the chemoattractant activity of the cleaved pro-inflammatory mediator is reduced or abrogated. Thus, for example, a functional variant of ScpA from *Streptococcus pyogenes* includes variant ScpA proteases that have the ability to specifically bind and irreversibly cleave the human C5a protein such that the chemoattractant capability of the cleaved protease is reduced or abrogated, and include ScpA proteases from *Streptococcus pyogenes* (SEQUENCE ID NO:2, 3, 4, 5) and other Streptococcal species. The term "variant" should be understood to mean proteins or polypeptides that have at least 70% sequence homology with the reference protease, and that are altered in respect of one or more amino acid residues. Preferably such alterations involve the insertion, addition, deletion and/or substitution of 20, 10, 5 or fewer amino acids, more preferably of 4 or fewer, even more preferably of 3 or fewer, most preferably of 1 or 2 amino acids only. Insertion, addition and substitution with natural and modified amino acids is envisaged. The variant may have conservative amino acid changes, wherein the amino acid being introduced is similar structurally, chemically, or functionally to that being substituted. Typically, proteins which have been altered by substitution or deletion of catalytically-important residues will be excluded from the term "variant". For any given protease enzyme, details of such catalytically-important residues will be well known to those skilled in the art. Generally, the variant will have at least 70% amino acid sequence homology, preferably at least 80% sequence homology, more preferably at least 90% sequence homology, and ideally at least 95%, 96%, 97%, 98% or 99% sequence homology with the reference protease. In this context, sequence homology comprises both sequence identity and similarity, i.e. a polypeptide sequence that shares 90% amino acid homology with wild-type bacterial mature C5a peptidase is one in which any 90% of aligned residues are either identical to, or conservative substitutions of, the corresponding residues in wild-type bacterial C5a peptidase. Substitution may be conservative or non-conservative substitution, and may involve use of natural amino acids or amino acid analogues.

The term "variant" is also intended to include chemical derivatives of a protease, i.e. where one or more residues of a protease is chemically derivatized by reaction of a functional side group. Also included within the term variant are protease molecules in which naturally occurring amino acid residues are replaced with amino acid analogues.

Proteins and polypeptides (including variants and fragments thereof) of and for use in the invention may be generated wholly or partly by chemical synthesis or by expression from nucleic acid. The proteins and peptides of and for use in the present invention can be readily prepared according to well-established, standard liquid or, preferably, solid-phase peptide synthesis methods known in the art (see, for example, J. M. Stewart et al).

In this specification, the term "inflammatory condition" means a condition in which the host mounts a response to an assault. Examples of inflammatory conditions include chronic or acute inflammatory conditions including sepsis, septic shock, systemic inflammatory response syndrome, multiple organ dysfunction syndrome, hyper-reactive airway disease, allergic reaction.

In a different aspect, the invention provides a method of attaching a molecule comprising a polyaminoacid sequence to a surface, in which the C-terminal of the protease enzyme comprises a first tag and a second tag located distally of the first tag and separated from the first tag by a spacer, and in which the support comprises a coordinated transition metal ion and one or more functional groups, and in which the first tag comprises a motif capable of covalently reacting with the one or functional groups, and wherein the second tag comprises a motif capable of interacting with the coordinated transition metal ion, the method comprising the step of reacting the molecule comprising a polyaminoacid sequence with the surface.

BRIEF DESCRIPTION OF THE DRAWINGS

The invention description below refers to the accompanying drawings, of which.

The diagram shows the components and blood flow route envisaged for the implementation of the invention. Blood is removed from the patient and fractionated into a high protein plasma fraction and a high blood cell fraction. The former is passed over the active material (immobilized enzyme) in the reaction chamber and then recombined with the latter before return to the patient. Components of the invention are labeled: 1 the overall invention, 2 the extracorporeal blood purification device, 3 blood withdrawal line, 4 patient arm, 5 blood return line, 6 pumping system, 7 blood separator, 8 reaction chamber, 9 cartridge housing blood separation chambers, 10a and 10b blood separation chambers, 11 biocompatible size restrictive semi-permeable membrane, 12 line delivering protein rich plasma to reaction chamber, 13 line delivering blood cell rich fraction to mixing chamber, 14 line delivering treated plasma to mixing chamber, 15 mixing chamber for blood reconstitution, 16 vessel housing active component of reaction chamber, 17 reactive material comprising immobilized enzyme irreversibly coupled to solid support material.

Figure 2:

FIG. 2 is; Activity of ScpA against the pro-inflammatory mediator C5a

Panel a shows SDS-PAGE analysis of C5a untreated (−) and treated (+) with ScpA Panel b shows the scissile bond in the C5a sequence confirmed by Mass Spec analysis of C5a cleaved with ScpA.

DETAILED DESCRIPTION OF AN ILLUSTRATIVE EMBODIMENT

Figure 1:
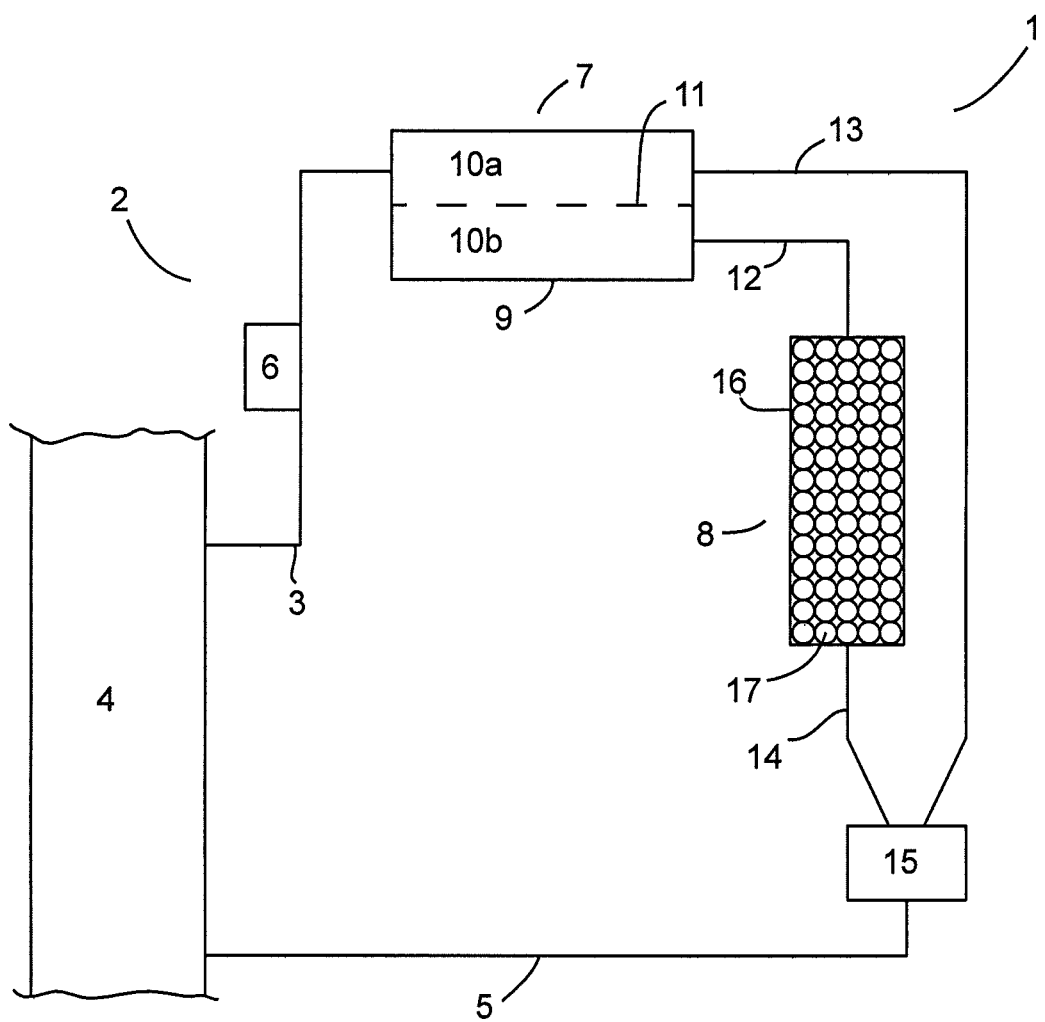
FIG. 1 is; Diagrammatic representation of blood purifying invention.

Referring to the FIG. 1, there is provided an apparatus for the extracorporeal treatment of blood according to the invention, and indicated generally by the reference numeral 1. The apparatus 1 comprises an extracorporeal blood circuit 2, having a feed line 3 for withdrawing blood from a patients arm 4 for treatment and a return line 5 for returning treated blood to the patient, and an adjustable pump 6 provided in the feed line for providing blood displacement within the blood circuit 2.

The apparatus also includes a blood separator 7 and a reaction chamber 8 in the circuit 2, the separator 7 being provided upstream of the reaction chamber 8. The separator comprises a cartridge 9 having two chambers 10a and 10b separated by a semi-permeable membrane 11 adapted to allow separation of blood proteins from blood cells. The whole blood passes from the patient to the first chamber 10a, where proteins in blood plasma pass into the second chamber 10b forming a protein rich plasma fraction in the second chamber and leaving blood cells in the first chamber 10a. A tube 12 is provided to transfer the thus-formed protein rich fraction plasma from the second chamber 10b to the reaction chamber 8 where it is treated. A further tube 13 is provided to transfer the cell rich fraction from the first chamber 10a to re-join with treated plasma distally of the reaction chamber 8 at a mixing chamber 15 where the two fractions are mixed prior to being returned to the patient via the whole blood return line 5.

The reaction chamber comprises a cylindrical vessel 16 filled with functionalized support material 17 containing the immobilized enzyme, thereby providing a large surface area for the treatment of the incoming plasma. The tube 12 feeds into a top of the cylindrical vessel 16, and the plasma filters through the cylinder before exiting the vessel through a tube 14.

Mesoporous silica (MPS) materials (including but not limited to MCM, SBA, MCF and PMO type materials) are prepared using a templated synthesis method. Ideally these particles will be monodispersed in nature. The particles will have a specific particle size in the range of 0.1-50 µm, contain nanopores with a final internal diameter in the range 8-12 nm and have a high surface area 300-800 $m^2\,g^{-1}$.

The surface characteristics of the silica nanocarriers will be modified with a range of functional groups (e.g. —NH2, —COOH, —SH) directly during synthesis of the material, or by post synthesis grafting to facilitate covalent coupling (through the poly-Gluamate or poly-Lysine or Cysteine residues respectively) of the enzyme to the surface after orientation specific adsorption.

The $Ni^{2+}$-modified MPS will be prepared by attachment of 3-iodo-trimethoxypropylsilane to the silicate surface followed by reaction with cyclam and incorporation of the metal ion. This is to generate immobilization of the protease in a controlled orientation.

In use, the extracorporeal blood circuit is connected to a patient, generally an arm of a patient, and the pump is actuated to withdraw blood from the patient and pump it through the circuit. The whole blood from the patient enters the separator 7 and is separated under pressure into the two fractions. The plasma fraction is pumped from the second chamber 10b to the reaction chamber 8 where the blood percolates through the functionalized cassette bed 17. In the reaction chamber, mediator in the plasma binds to the protease enzyme that is immobilized to the support material, and is cleaved into an inactive form that is released back into the plasma leaving the immobilized enzyme free for another reaction. As a result of the plasma passing through the reaction chamber, the concentration of functional mediator in the plasma is significantly reduced. The thus treated plasma is then pumped to the mixing chamber 15 where it rejoins with the cell rich fraction to form whole blood that is significantly depleted of active mediator protein. The whole blood is returned to the patient via the return line 5.

It will be appreciated that the use of a separator to filter the blood prior to treatment is optional, and that the treatment of whole blood in the reaction chamber forms part of the invention.

EXPERIMENTAL

Materials and Methods

C5a Peptidase Activity Assays

Recombinant C5a was produced as an N-term His-tagged fusion (HT-05a) in accordance with the method of Toth et al., and chemoattractant activity was verified in an under-agarose migration assay (data not shown). The C5a-ase activity of ScpA was demonstrated in reactions consisting of 42 nM ScpA with 37 µM HT-05a, in 50 mM Tris/HCl (pH 7.5), 100 mM NaCl, and 5 mM $CaCl_2$ for 30 min at 20° C. The observed C5a-ase activity was independent of the presence of Complete Mini EDTAfree inhibitor cocktail (Roche). Matrix-assisted laser desorption ionization time-of-flight mass spectrometry analysis of cleaved HT-C5a was performed.

Results

The activity assay showed that the ScpA cleaved C5a at a single site (FIG. 2*a*). MS analysis indicated a loss of 830 Da, consistent with the removal of seven residues from the C terminal (FIG. 2*b*) which removes chemoattractant capabilities.

The invention is not limited to the embodiments hereinbefore described which may be varied in construction and detail without departing from the spirit of the invention.

REFERENCES

Brown C K, Gu Z Y, Matsuka Y V, Purushothaman S S, Winter L A, Cleary P P, Olmsted S B, Ohlendorf D H, Earhart C A. Structure of the streptococcal cell wall C5a peptidase. Proc Natl Acad Sci USA. 2005 Dec. 20; 102(51):18391-6. Epub 2005 Dec. 12. PubMed PMID: 16344483; PubMed Central PMCID: PMC1317908.

Fritzer A, Noiges B, Schweiger D, Rek A, Kungl A J, von Gabain A, Nagy E, Meinke A L. Chemokine degradation by the Group A streptococcal serine proteinase ScpC can be reconstituted in vitro and requires two separate domains. Biochem J. 2009 Aug. 27; 422(3):533-42. doi: 10.1042/BJ20090278. PubMed PMID: 19552626.

Kaur S J, Nerlich A, Bergmann S, Rohde M, Fulde M, Zähner D, Hanski E, Zinkernagel A, Nizet V, Chhatwal G S, Talay S R. The CXC chemokine-degrading protease SpyCep of *Streptococcus pyogenes* promotes its uptake into endothelial cells. J Biol Chem. 2010 Sep. 3; 285(36):27798-805. doi: 10.1074/jbc.M109.098053. Epub 2010 Jun. 18. PubMed PMID: 20562101; PubMed Central PMCID: PMC2934647.

Zinkernagel A S, Timmer A M, Pence M A, Locke J B, Buchanan J T, Turner C E, Mishalian I, Sriskandan S, Hanski E, Nizet V. The IL-8 protease SpyCEP/ScpC of group A *Streptococcus* promotes resistance to neutrophil killing. Cell Host Microbe. 2008 Aug. 14; 4(2):170-8. doi: 10.1016/j.chom.2008.07.002. PubMed PMID: 18692776; PubMed Central PMCID: PMC2631432.

Sjölinder H, Lövkvist L, Plant L, Eriksson J, Aro H, Jones A, Jonsson A B. The ScpC protease of *Streptococcus pyogenes* affects the outcome of sepsis in a murine model. Infect Immun. 2008 September; 76(9):3959-66. doi: 10.1128/IAI.00128-08. Epub 2008 Jun. 23. PubMed PMID: 18573900; PubMed Central PMCID: PMC2519448.

Hidalgo-Grass C, Mishalian I, Dan-Goor M, Belotserkovsky I, Eran Y, Nizet V, Peled A, Hanski E. A streptococcal protease that degrades CXC chemokines and impairs bacterial clearance from infected tissues. EMBO J. 2006 Oct. 4; 25(19):4628-37. Epub 2006 Sep. 14. PubMed PMID: 16977314; PubMed Central PMCID: PMC1589981.

Matheson N R, Potempa J, Travis J. Interaction of a novel form of *Pseudomonas aeruginosa* alkaline protease (aeruginolysin) with interleukin-6 and interleukin-8. Biol Chem. 2006 July; 387(7):911-5. PubMed PMID: 16913841.

J. M. Stewart and J. D. Young, Solid Phase Peptide Synthesis, 2nd edition, Pierce Chemical Company, Rockford, Ill. (1984), in M. Bodanzsky and A. Bodanzsky, The Practice of Peptide Synthesis, Springer Verlag, New York (1984).

Toth, M. J., Huwyler, L., Boyar, W. C., Braunwalder, A. F., Yarwood, D., Hadala, J., Haston, W. O., Sills, M. A., Seligmann, B., Galakatos, N. The pharmacophore of the human C5a anaphylatoxin. Protein Sci. 3:1159-1168, 1994.

What is claimed is:

1. An apparatus for the extracorporeal treatment of blood comprising:
an extracorporeal blood circuit (2);
a pump (6) configured to provide fluid displacement within the extracorporeal blood circuit; and
a reaction chamber (8) connected to the extracorporeal blood circuit and configured to receive blood or a human C5a-containing blood fraction from the circuit and treat the blood or human C5a-containing blood fraction,
characterized in that the reaction chamber comprises a protease enzyme irreversibly immobilized to a support, in which the protease enzyme is specific for, and capable of irreversibly cleaving, human C5a present in the blood or blood fraction such that the chemoattractant capability of the cleaved human C5a is reduced, wherein the abundance of the functional human C5a in the treated blood or blood fraction is less than that in the untreated blood or blood fraction, and the protease enzyme is a recombinant bacterial C5a protease selected from the group consisting of SEQ ID NO: 4 and SEQ ID NO: 5.

2. An apparatus as claimed in claim 1 further including separating means (7) adapted to separate the blood into a C5a-containing fraction and a non-C5a containing fraction, wherein the reaction chamber receives the C5a-containing fraction.

3. An apparatus as claimed in claim 2 further including means (15) configured to recombine the treated C5a-containing fraction with the non-C5a containing fraction.

4. An apparatus as claimed in claim 1, wherein a C-terminal of the protease enzyme comprises a first tag and a second tag located distally of the first tag and separated from the first tag by a spacer, the support comprises a coordinated transition metal ion and one or more functional groups for covalent coupling of the protease enzyme to the support, the first tag comprises a motif covalently coupled to the one or more functional groups, and the second tag comprises a motif capable of interacting with the coordinated transition metal ion.

5. An apparatus as claimed in claim 4, wherein the support comprises a $Ni^{2+}$-modified mesoporous silica material.

6. An apparatus as claimed in claim 4, wherein the first tag is selected from poly-lysine, poly-glutamate, and poly-cysteine, and the second tag comprises poly-histidine.

7. An apparatus as claimed in claim 6, wherein the support comprises a $Ni^{2+}$-modified mesoporous silica material.

8. An apparatus as claimed in claim 1, wherein the support comprises a multiplicity of beads (17) and the protease enzyme is irreversibly immobilized to a surface of the beads.

9. An apparatus as claimed in claim 1 for use in a method for the ex-vivo treatment of blood in a human with sepsis.

10. An apparatus for treating human blood or a C5a-containing blood fraction, the apparatus comprising a protease enzyme irreversibly bound to a support, in which the protease enzyme is specific for, and capable of irreversibly cleaving, human C5a present in the blood or blood fraction such that the chemoattractant capability of the cleaved human C5a is reduced, wherein the protease enzyme is a recombinant bacterial C5a protease selected from the group consisting of SEQ ID NO: 4 and SEQ ID NO: 5.

11. An apparatus as claimed in claim 10, wherein a C-terminal of the protease enzyme comprises a first tag and a second tag located distally of the first tag and separated from the first tag by a spacer, the support comprises a coordinated metal ion and one or more functional groups for covalent coupling of the protease enzyme to the support, the first tag comprises a motif covalently coupled to the one or more functional groups, and the second tag comprises a motif capable of interacting with the coordinated metal ion.

12. An apparatus as claimed in claim 11, wherein the first tag is selected from poly-lysine, poly-glutamate, and poly-cysteine, and the second tag comprises poly-histidine.

13. A protease enzyme comprising the sequence of A-B-C-D, in which A is selected from the group consisting of SEQ ID NO: 4 and SEQ ID NO: 5, B is a poly-lysine, poly-cysteine, or poly-glutamate motif, C is a spacer, and D is a poly-histidine motif.

* * * * *